United States Patent
Miyawaki

(10) Patent No.: US 10,356,907 B2
(45) Date of Patent: Jul. 16, 2019

(54) ENDOSCOPE, ELECTRONIC UNIT AND METHOD FOR MANUFACTURING ELECTRONIC UNIT

(71) Applicant: OLYMPUS CORPORATION, Tokyo (JP)

(72) Inventor: Takahide Miyawaki, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 17 days.

(21) Appl. No.: 15/893,892

(22) Filed: Feb. 12, 2018

(65) Prior Publication Data

US 2018/0168046 A1  Jun. 14, 2018

Related U.S. Application Data

(63) Continuation of application No. PCT/JP2015/074639, filed on Aug. 31, 2015.

(51) Int. Cl.
*A61B 1/00* (2006.01)
*H05K 1/11* (2006.01)
(Continued)

(52) U.S. Cl.
CPC ............ *H05K 1/181* (2013.01); *A61B 1/0011* (2013.01); *A61B 1/042* (2013.01); *G02B 23/24* (2013.01);
(Continued)

(58) Field of Classification Search
None
See application file for complete search history.

(56) References Cited

U.S. PATENT DOCUMENTS 5,990,546 A * 11/1999 Igarashi ............... H01L 23/3121
257/700
6,111,306 A * 8/2000 Kawahara ........... H01L 21/4853
257/666
(Continued)

FOREIGN PATENT DOCUMENTS

JP   H06-013541 A   1/1994
JP   2010-232333 A  10/2010
(Continued)

OTHER PUBLICATIONS

International Search Report dated Nov. 17, 2015 issued in PCT/JP2015/074639.

*Primary Examiner* — Fernando Alcon
(74) *Attorney, Agent, or Firm* — Scully, Scott, Murphy & Presser, P.C.

(57) ABSTRACT

An endoscope includes an image pickup unit at a distal end portion of an insertion portion, the image pickup unit includes a chip part provided with a first electrode pad and a second electrode pad, an image pickup device provided with a third electrode pad and a wiring board including a flying lead, the flying lead is inserted into a gap between the chip part and the image pickup device, the first electrode pad and the flying lead are bonded together via a first bump, a bonded portion between the first electrode pad and the flying lead is sealed with first sealing resin, the second electrode pad and the third electrode pad are bonded together via a second bump which is higher than the first bump and sealed with second sealing resin having a Young's modulus lower than a Young's modulus of the first sealing resin.

14 Claims, 7 Drawing Sheets

(51) Int. Cl.
*H05K 1/14* (2006.01)
*H05K 1/18* (2006.01)
*H05K 3/28* (2006.01)
*A61B 1/04* (2006.01)
*H05K 3/32* (2006.01)
*G02B 23/24* (2006.01)
*H01L 25/07* (2006.01)
*H01L 25/18* (2006.01)
*H04N 5/225* (2006.01)
*H01L 25/065* (2006.01)
*H05K 3/34* (2006.01)

(52) U.S. Cl.
CPC ..... *G02B 23/2423* (2013.01); *G02B 23/2446* (2013.01); *G02B 23/2484* (2013.01); *H01L 25/065* (2013.01); *H01L 25/07* (2013.01); *H01L 25/18* (2013.01); *H04N 5/2253* (2013.01); *H05K 1/111* (2013.01); *H05K 3/284* (2013.01); *H05K 3/32* (2013.01); *A61B 1/00096* (2013.01); *H01L 2224/16225* (2013.01); *H01L 2224/73253* (2013.01); *H04N 2005/2255* (2013.01); *H05K 1/14* (2013.01); *H05K 1/141* (2013.01); *H05K 3/3426* (2013.01); *H05K 2201/1028* (2013.01); *H05K 2201/1031* (2013.01); *H05K 2201/10151* (2013.01); *H05K 2201/10977* (2013.01); *H05K 2203/0285* (2013.01); *Y02P 70/611* (2015.11)

(56) References Cited

U.S. PATENT DOCUMENTS

| | | | |
|---|---|---|---|
| 6,881,661 B2 * | 4/2005 | Nishibe | H01L 21/76802 |
| | | | 257/E21.579 |
| 7,193,328 B2 * | 3/2007 | Suzuki | H01L 23/4985 |
| | | | 257/668 |
| 2015/0014805 A1 | 1/2015 | Yamada | |

FOREIGN PATENT DOCUMENTS

| | | |
|---|---|---|
| JP | 5106460 B2 | 12/2012 |
| JP | 2013-219468 A | 10/2013 |
| JP | 2014-108282 A | 6/2014 |
| WO | WO 2013/150813 A1 | 10/2013 |

* cited by examiner

ENDOSCOPE, ELECTRONIC UNIT AND METHOD FOR MANUFACTURING ELECTRONIC UNIT

CROSS REFERENCE TO RELATED APPLICATION

This application is a continuation application of PCT/JP2015/074639 filed on Aug. 31, 2015, the entire contents of which are incorporated herein by this reference.

BACKGROUND OF INVENTION

1. Field of the Invention

The present invention relates to an endoscope including an image pickup unit provided with a first chip part, a second chip part such as an image pickup device disposed opposite to the first chip part and a wiring board, from an end face of which a flying lead protrudes, an electronic unit provided with a first chip part, a second chip part disposed opposite to the first chip part and a wiring board, from an end face of which a flying lead protrudes, and a method for manufacturing the electronic unit.

2. Description of the Related Art

An image pickup unit provided with an ultra-small image pickup device is being developed to reduce the diameter/length of a distal end portion of an endoscope. The image pickup device is provided with an electrode pad to supply a drive signal or the like and an electrode pad to output an image pickup signal. It is not easy to directly bond a signal cable to the electrode pad of the image pickup device because doing so may damage the image pickup device. Thus, for example, a chip part for rewiring and a wiring board on which an electronic part is mounted are disposed between the image pickup device and the signal cable.

Note that Japanese Patent Application Laid-Open Publication No. 6-13541 discloses a three-dimensional multichip semiconductor device which is miniaturized by arranging a wiring board mounted with a semiconductor chip on a wiring board on which a semiconductor chip is mounted via a first bump and bonding the wiring boards together via a second bump higher than the first bump.

SUMMARY OF THE INVENTION

An endoscope according to an embodiment of the present invention is an endoscope provided with an image pickup unit at a distal end of an insertion portion, the image pickup unit including a chip part, on a principal surface of which a first electrode pad and a second electrode pad are disposed, an image pickup device, a back surface opposite to a light-receiving surface of which is disposed opposite to the principal surface of the chip part and on the back surface of which a third electrode pad is disposed and a wiring board including a flying lead that protrudes from an end face, in which the flying lead is inserted into a gap between the chip part and the image pickup device, the first electrode pad and the flying lead are bonded together via a first bump and a bonded portion between the first electrode pad and the flying lead is sealed with first sealing resin, and the second electrode pad and the third electrode pad are bonded together via a second bump which is higher than the first bump, and a space of the gap not sealed with the first sealing resin is sealed with second sealing resin having a Young's modulus lower than a Young's modulus of the first sealing resin.

An electronic unit according to another embodiment of the present invention is an electronic unit including a first chip part, on a principal surface of which a first electrode pad and a second electrode pad are disposed, a second chip part, a back surface opposite to a front surface of which is disposed opposite to the principal surface of the first chip part and on the back surface of which a third electrode pad is disposed, and a wiring board including a flying lead that protrudes from an end face, in which the flying lead is inserted into a gap between the first chip part and the second chip part, the first electrode pad and the flying lead are bonded together via a first bump and a bonded portion between the first electrode pad and the flying lead is sealed with first sealing resin, and the second electrode pad and the third electrode pad are bonded together via a second bump which is higher than the first bump and a space of the gap not sealed with the first sealing resin is sealed with second sealing resin.

A method for manufacturing an electronic unit according to a further embodiment of the present invention includes a step of manufacturing a first chip part, on a principal surface of which a first electrode pad and a second electrode pad are disposed, a second chip part on a back surface opposite to a front surface of which a third electrode pad is disposed and a wiring board including a flying lead that protrudes from an end face, a step of bonding the first electrode pad of the first chip part and the flying lead of the wiring board via a first bump, a step of sealing a bonded portion between the first electrode pad and the flying lead with first sealing resin, a step of curing the first sealing resin at a first temperature, a step of disposing the principal surface of the first chip part and the back surface of the second chip part opposite to each other and bonding the second electrode pad and the third electrode pad via a second bump which is higher than the first bump, a step of injecting second sealing resin into a gap between the principal surface of the first chip part and the back surface of the second chip part and a step of curing the second sealing resin at a temperature lower than the first temperature and lower than a glass transition temperature of the first sealing resin.

DETAILED DESCRIPTION OF THE PREFERRED EMBODIMENTS

First Embodiment

Figure 1:
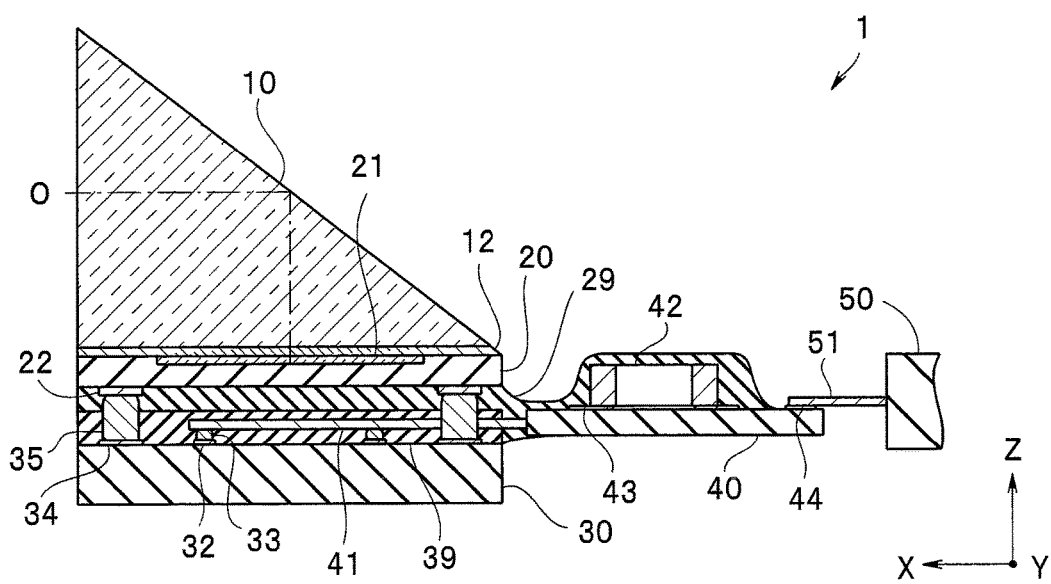
FIG. 1 is a cross-sectional view of an image pickup unit according to a first embodiment.
Figure 2:
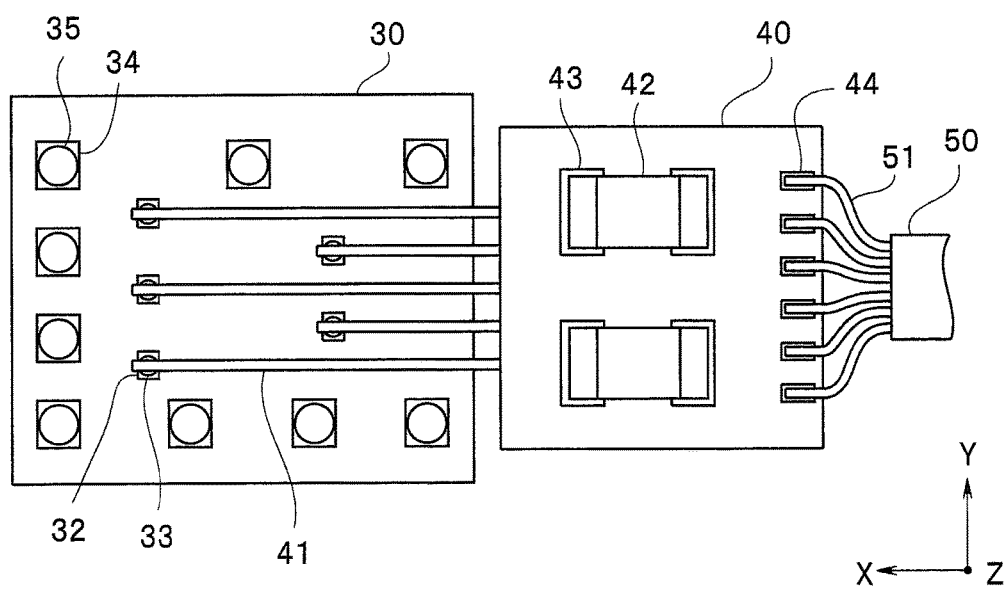
FIG. 2 is a top view of part of the image pickup unit of the first embodiment.
Figure 3:
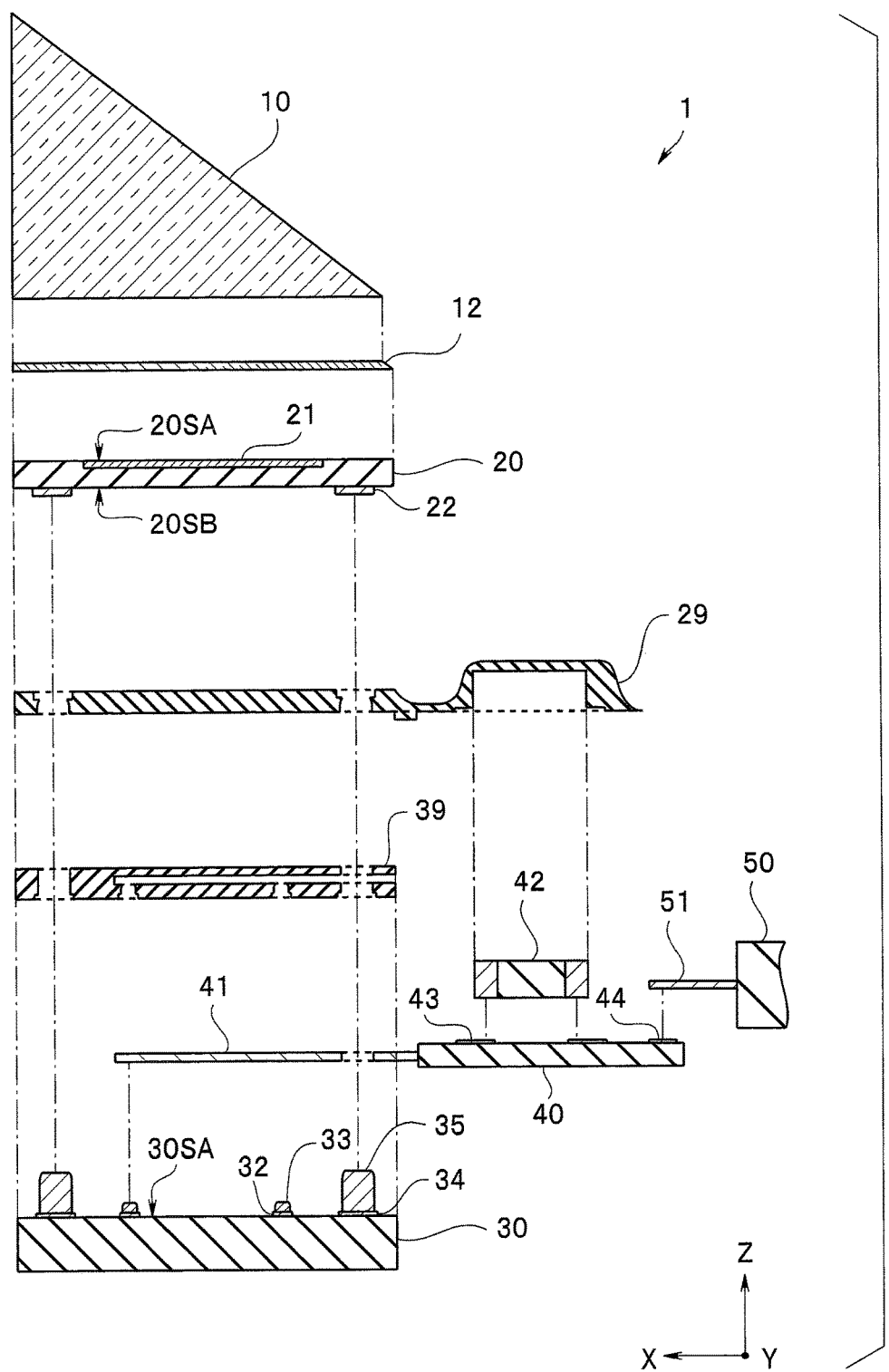
FIG. 3 is an exploded view of the image pickup unit of the first embodiment.

As shown in FIG. 1 to FIG. 3, an image pickup unit 1 according to the present embodiment is a so-called horizontal image pickup unit provided with a prism 10, an image pickup device 20, a wiring chip 30, a wiring board 40 and a signal cable 50.

In the following description, it should be noted that drawings based on the respective embodiments are schematic ones and a thickness-width relationship in the respective components, a thickness ratio and relative angles or the like among the respective components are different from the reality, and there may be a case where components with different dimensional relationships or ratios among the drawings are included. Illustrations of some components may be omitted.

The wiring chip 30 which is a first chip part is provided with a plurality of first electrode pads 32 and a plurality of second electrode pads 34 disposed on a principal surface 30SA. The wiring chip 30 includes a wiring function that electrically connects the first electrode pad 32 and the second electrode pad 34.

The image pickup device 20 which is a second chip part is made of a semiconductor such as silicon. The image pickup device 20 is a CCD or CMOS image sensor in which a light-receiving section 21 is formed using a publicly known semiconductor manufacturing technique. A plurality of third electrode pads 22 connected to the light-receiving section 21 via a through wiring (not shown) or the like are disposed on a back surface 20SB opposite to a light-receiving surface (front surface) 20SA.

The prism 10 which is an optical member is disposed on the light-receiving surface 20SA of the image pickup device 20 via a transparent adhesive layer 12. Note that the prism 10 is not an indispensable component of the image pickup unit 1 and cover glass may be disposed instead of the prism or cover glass may be disposed below the prism 10. In the case of an image pickup device in which a plurality of microlenses are disposed on the light-receiving section 21, an optical member may be disposed around the light-receiving section 21 via a frame-shaped light-shielding adhesive layer.

The wiring board 40 includes a plurality of flying leads 41 that protrude from an end face. The flying lead 41 is also called an "inner lead" among lead frames, and is a bar-shaped metal conductor formed by selectively detaching an insulating layer or the like around the wiring of the wiring board 40. For example, the flying lead 41 is 250 μm long, 20 μm thick and 50 μm wide. An electrode pad 43 on which an electronic part 42 such as a chip capacitor is mounted and an electrode pad 44 to which a conductive wire 51 of the signal cable 50 is connected are disposed on the wiring board 40. The wiring board may be a double-sided wiring board, a multilayer wiring board or a part-incorporating wiring board.

In the image pickup unit 1, the principal surface 30SA of the wiring chip 30 and the back surface 20SB of the image pickup device 20 are disposed opposite to each other. The flying lead 41 of the wiring board 40 is inserted into a gap between the principal surface 30SA of the wiring chip 30 and the back surface 20SB of the image pickup device 20.

The first electrode pad 32 and the flying lead 41 are bonded together via a first bump 33. The second electrode pad 34 and the third electrode pad 22 are bonded together via a second bump 35. The second bump 35 is higher than the first bump 33, and thereby defines the length of the gap between the wiring chip 30 and the image pickup device 20. For example, the height of the first bump 33 is 5 μm to 50 μm and the height of the second bump 35 is 20 μm to 150 μm.

The bonded portion between the first electrode pad 32 and the flying lead 41 is sealed with first sealing resin 39. Note that the first sealing resin 39 more preferably covers and seals the flying lead 41. The space of the gap between the wiring chip 30 and the image pickup device 20 not sealed with the first sealing resin 39 is sealed with second sealing resin 29.

When the chip part and the wiring board are disposed, the length or thickness of the image pickup unit may increase, which may hamper the diameter/length reduction of the distal end portion. When the wiring board and the chip part are connected together via the flying lead of the wiring board, if stress is applied in the manufacturing step, the bonded portion may be detached. Especially when the flying lead is bent after bonding, strong stress is applied to the bonded portion, and so the bonded portion may be detached.

In the image pickup unit 1, the bonded portion between the first electrode pad 32 and the flying lead 41, that is, the distal end portion of the flying lead 41 is inserted into the gap between the wiring chip 30 and the image pickup device 20. Therefore, the image pickup unit 1 is short. Moreover, the bonded portion is fixed by the first sealing resin and the second sealing resin. Thus, the bonded portion has high bonding reliability and even when stress is applied from outside, the bonded portion is never detached. Therefore, the image pickup unit 1 exhibits high manufacturing yield.

Note that in order to further increase the bonding strength between the first electrode pad 32 and the flying lead 41, the first sealing resin 39 is preferably hard resin, for example, resin having a Young's modulus of 10 GPa or more. In contrast, the second sealing resin 29 is preferably soft resin, for example, resin having a Young's modulus of less than 10 GPa in order to relax stress caused by a difference in thermal expansion coefficient between the image pickup device 20 and the wiring chip 30.

<Method for Manufacturing Image Pickup Unit>

Figure 4:
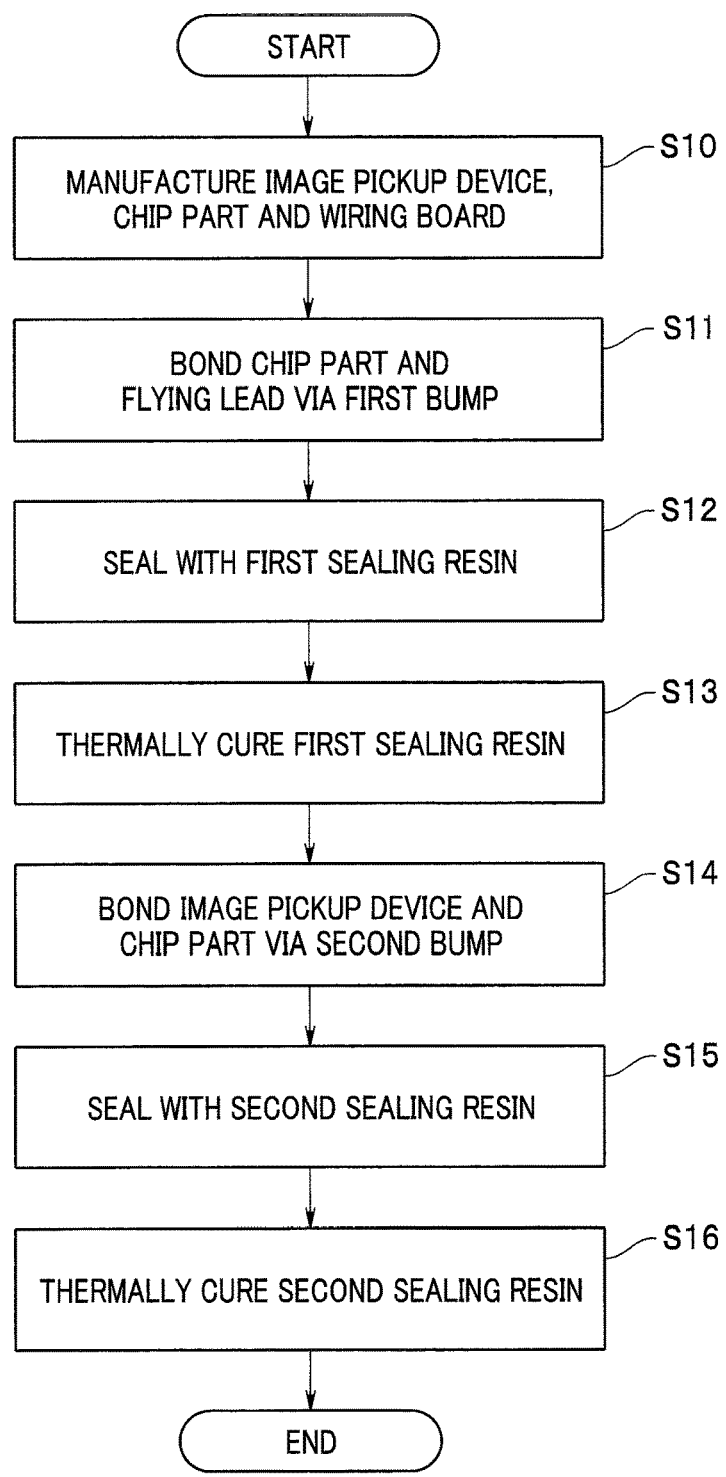
FIG. 4 is a flowchart for describing a method for manufacturing the image pickup unit of the first embodiment.

Next, a method for manufacturing the image pickup unit will be described along a flowchart in FIG. 4.

<Step S10>

The image pickup device 20, the wiring chip 30 and the wiring board 40 are manufactured.

The image pickup device 20 is manufactured by cutting a silicon wafer in which a plurality of light-receiving sections 21 and the like are formed. The light-receiving section 21, a peripheral circuit section (not shown), a through wiring (not shown) and the electrode pad 22 are formed in the image pickup device 20.

In a plan view, the wiring chip 30 has substantially the same size as the size of the image pickup device 20 and includes the first bump 33 disposed on the first electrode pad 32 and the second bump 35 disposed on the second electrode pad 34. The first electrode pad 32 and the second electrode pad 34 are electrically connected together via a wiring (not shown). An electronic part such as a capacitor or resistor may be disposed on the back surface opposite to the principal surface 30SA of the wiring chip 30. Furthermore, the wiring chip 30 may be a semiconductor chip in which a semiconductor circuit or the like is formed.

The first bump 33 and the second bump 35 are Au-stud bumps, plating bumps, ball bumps, printing bumps or the like. The manufacturing method of the first bump 33 may be different from that of the second bump 35. The height of the second bump 35 is greater than the height of the first bump 33 and the height of the second bump 35 defines the length of the gap between the image pickup device 20 and the wiring chip 30.

Note that the second bump 35 is preferably a plated bump, a multi-stage bump or a ball bump because it is possible to form a plurality of such bumps of great height easily and accurately to a predetermined height. In contrast, the first bump 33 is preferably a stud bump which is easy to manufacture.

<Step S11>

The first electrode pad 32 of the wiring chip 30 and the flying lead 41 of the wiring board 40 are bonded together via the first bump 33.

When the first bump 33 is an Au-stud bump, a plurality of flying leads 41 and a plurality of first bumps 33 are simultaneously bonded through, for example, ultrasound bonding. Bonding may be solder bonding.

<Step S12>

The bonded portion between the first electrode pad 32 and the flying lead 41 is sealed with the first sealing resin 39. Note that the first sealing resin 39 preferably covers substantially the whole principal surface 30SA of the wiring chip 30 except an upper part of the second electrode pad 34.

The first sealing resin 39 is, for example, liquid thermosetting resin before curing, for example, epoxy resin. As has already been described, in order to increase bonding strength of the bonded portion between the first electrode pad 32 and the flying lead 41, the first sealing resin 39 is preferably hard resin, resin having a Young's modulus of 10 GPa or higher, and more preferably 20 GPa or higher. As will be described later, the sealing resin 39 preferably has a glass transition temperature TG higher than a curing temperature $T2$ of the second sealing resin 29.

<Step S13>

The first sealing resin is cured at a first temperature $T1$. The curing temperature $T1$ is, for example, 100° C. to 160° C.

<Step S14>

The principal surface 30SA of the wiring chip 30 and the back surface 20SB of the image pickup device 20 are disposed opposite to each other, and the second electrode pad 34 and the third electrode pad 22 are, for example, press bonded via the second bump 35. Bonding may be solder bonding.

The flying lead 41 bonded to the wiring chip 30 remains inserted in the gap between the wiring chip 30 and the image pickup device 20.

The height of the second bump 35 is greater than the height of the first bump 33. Strictly speaking, the height of the second bump 35 is configured to be greater than the sum of the height of the first bump 33, the thickness of the flying lead 41 and the thickness of the first sealing resin 39 covering the top of the flying lead 41.

<Step S15>

The second sealing resin 29 is inserted into the gap between the principal surface 30SA of the wiring chip 30 and the back surface 20SB of the image pickup device 20. Note that the second sealing resin 29 may seal up to the wiring board 40.

The second sealing resin 29 is in a liquid state before curing and fills the gap through interfacial tension without generating any cavity in the gap. The second sealing resin 29 is preferably relatively soft resin, for example, resin having a Young's modulus of lower than 10 GPa from the standpoint of stress relaxation and a Young's modulus of 5 GPa or lower is particularly preferable.

<Step S16>

The second sealing resin 29 is subjected to a curing process at a second temperature $T2$. The second temperature $T2$ is preferably lower than the first temperature $T1$ and lower than the glass transition temperature TG of the first sealing resin 39. Using the second sealing resin 29 under the above-described condition prevents detachment of the bonded portion between the first electrode pad 32 and the flying lead 41 during thermal curing of the second sealing resin 29.

For example, when the first sealing resin 39 is epoxy resin A having a curing temperature $T1$ of 160° C. and a glass transition temperature TG of 150° C., silicone resin having a curing temperature $T2$ of 95° C. or epoxy resin B having a curing temperature $T2$ of 100° C. is used as the second sealing resin 29.

The first sealing resin 39 and the second sealing resin 29 are selected from various kinds of thermosetting resin such as phenol resin, urea resin, melamine resin, epoxy resin, silicone resin and polyester resin. Filler such as glass fiber or particles having high thermal conductivity such as silicon particles may be added to resin.

Note that a selection of the first sealing resin 39 and the second sealing resin 29 according to the curing temperature is relative, and so when, for example, the first sealing resin 39 is epoxy resin C having a curing temperature $T1$ of 90° C. and a glass transition temperature TG of 80° C., it is not preferable to use silicone resin having a curing temperature $T2$ of 95° C. as the second sealing resin 29.

In the case where the second bump 35 is a solder bump having a bonding temperature $T3$, the glass transition temperature TG of the first sealing resin 39 is preferably equal to or higher than a bonding temperature $T3$.

Since the bonding strength between the first electrode pad 32 and the flying lead 41 is high and both parts are never detached from each other during manufacturing, the method for manufacturing the image pickup unit 1 is easy to handle and achieves a high manufacturing yield.

Second Embodiment

Next, an image pickup unit 1A according to a second embodiment will be described. Since the image pickup unit 1A is similar to the image pickup unit 1 and has the same effects, the same components are assigned the same reference numerals and description will be omitted.

Figure 5:
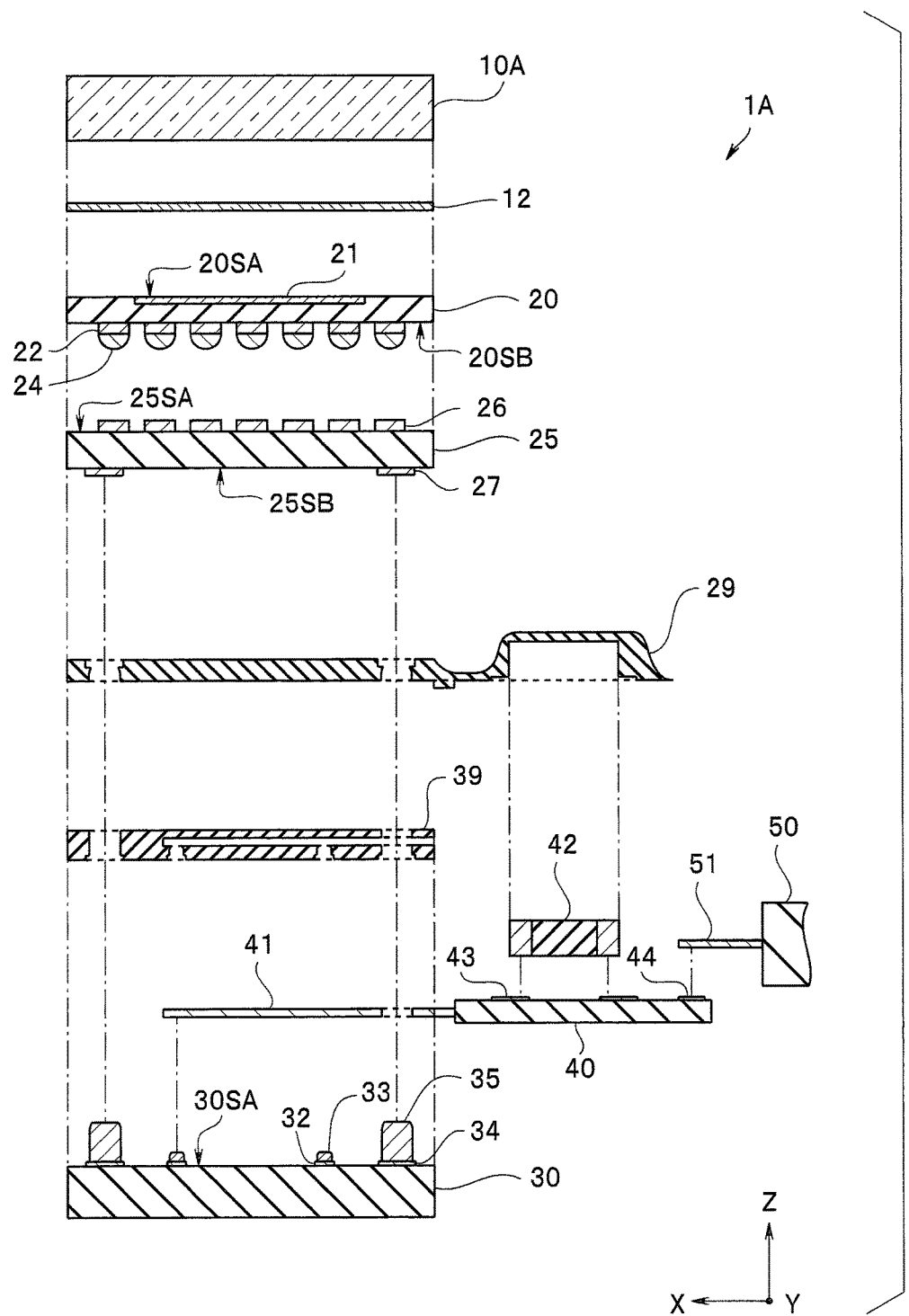
FIG. 5 is an exploded view of an image pickup unit according to a second embodiment.

As shown in FIG. 5, in the image pickup unit 1A, a wiring chip 25 which can be regarded as the second chip part is disposed between the wiring chip 30 which is the first chip part and the image pickup device 20. That is, the image pickup device 20 is disposed on a first principal surface (front face) 25SA of the wiring chip 25 and cover glass 10A is bonded to the light-receiving surface 20SA of the image pickup device 20 via the adhesive layer 12.

The wiring chip 25 is a wiring chip such as an interposer and electrically connects an electrode 26 on a first principal surface (front face) 25SA and an electrode 27 on a second principal surface (back surface) 25SB. The image pickup device 20 and the wiring chip 25 are bonded together via, for example, a solder bump. The wiring chips 30 and 25 each may be a semiconductor chip in which a semiconductor circuit is formed.

Third Embodiment

Next, an image pickup unit 1B according to a third embodiment will be described. Since the image pickup unit 1B is similar to the image pickup unit 1 and has the same effects, the same components are assigned the same reference numerals and description will be omitted.

Figure 6:
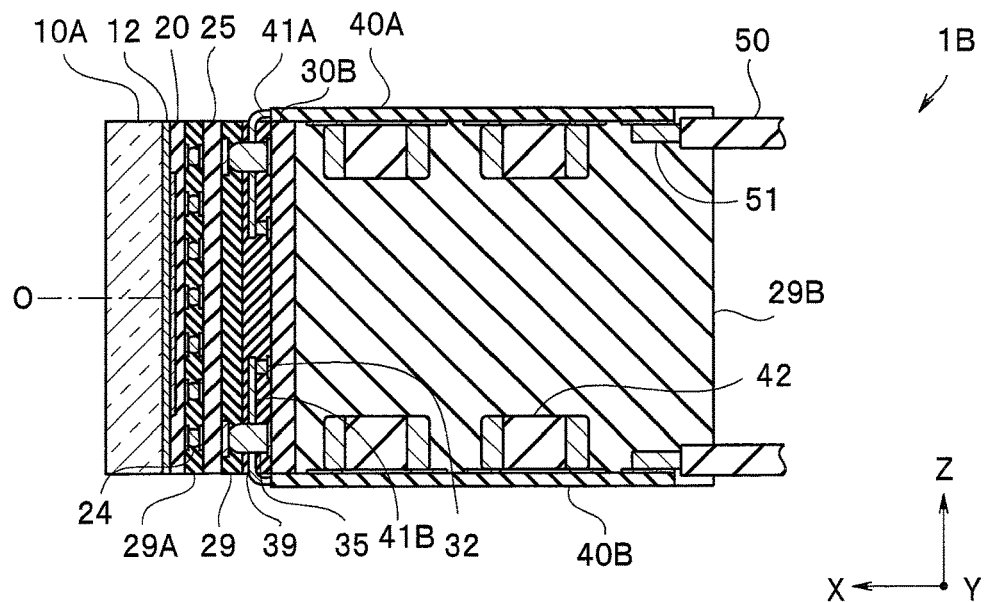
FIG. 6 is a cross-sectional view of an image pickup unit according to a third embodiment.
Figure 7:
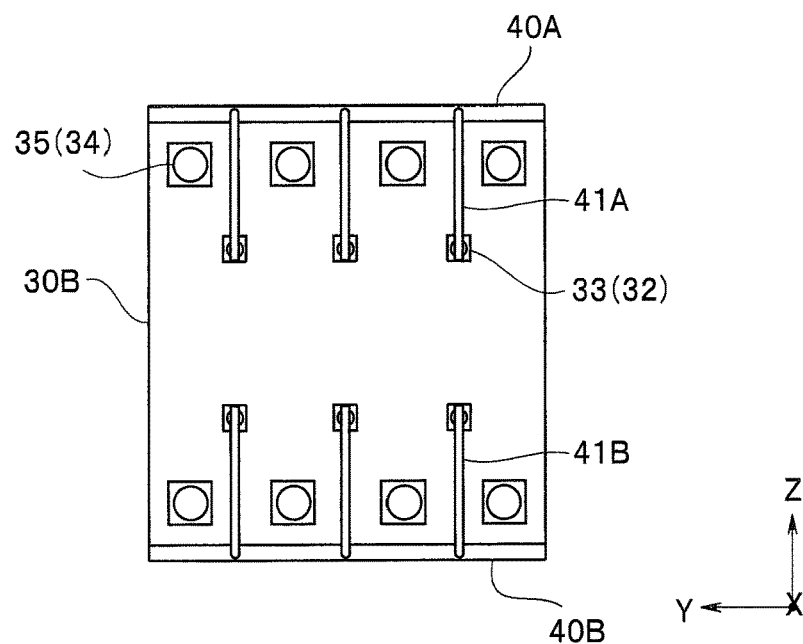
FIG. 7 is a top view of part of the image pickup unit of the third embodiment.

As shown in FIG. 6 and FIG. 7, in the image pickup unit 1B, flying leads 41A and 41B of two wiring boards 40A and 40B are respectively inserted and fixed in a gap between the wiring chip 25 and the wiring chip 30B.

The image pickup unit 1B is a so-called vertical image pickup unit with the flying leads 41A and 41B being bent at a right angle outside the gap and principal surfaces of the wiring boards 40A and 40B being disposed perpendicular to the light-receiving surface of the image pickup device 20.

The space between the wiring boards 40A and 40B which are disposed opposite to each other is sealed with sealing resin 29B. Electronic parts 42 mounted on the wiring boards 40A and 40B are disposed inside. Thus, the image pickup unit 1B has a smaller outside diameter.

Note that the bending angle of the flying lead 41A or the like need not be precisely 90 degrees, and may be, for example, less than 90 degrees. Even for an image pickup unit having only one wiring board, the flying lead may be bent as in the case of the image pickup unit 1B to reduce the diameter.

When the flying lead is bent, large stress is applied to the bonded portion of the flying lead. However, in the image pickup unit 1B, the flying lead is inserted and fixed in the gap between the wiring chip 25 and the wiring chip 30B, and so it is unlikely that the bonded portion will be detached during manufacturing.

<Endoscope>

Note that the image pickup units 1, 1A and 1B (hereinafter referred to as "image pickup unit 1 or the like") according to the embodiments have been described so far. Since the image pickup unit 1 or the like is small, the image pickup unit 1 or the like can be suitably used as an image pickup unit for an endoscope.

Figure 8:
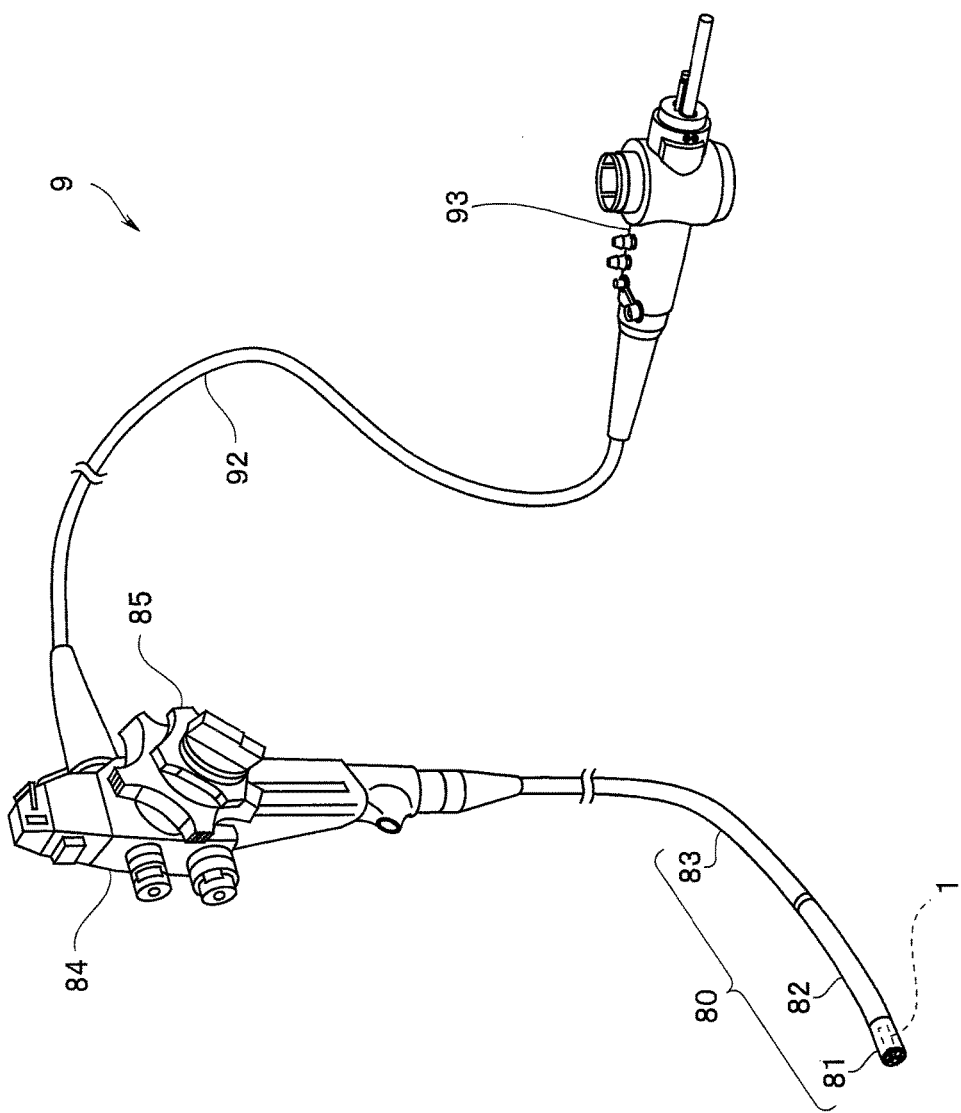
FIG. 8 is a perspective view of an endoscope according to an embodiment.

An endoscope 9 according to the embodiment provided with the image pickup unit 1 or the like will be described simply using FIG. 8. An insertion portion 80 of the endoscope 9 is constructed of a distal end portion 81, a bending portion 82 configured to change the direction of the distal end portion 81 and a flexible portion 83 having flexibility and connected from the bending portion 82. An operation portion 84 is provided with an angle knob 85 configured to operate the bending portion 82. A connector 93 disposed at a proximal end portion of a universal cord 92 is connected to a processor (not shown).

The endoscope 9 according to the embodiment is provided with the image pickup unit 1 or the like at the distal end portion 81 of the insertion portion 80. For example, the image pickup unit 1 is an image pickup unit provided with a chip part, on a principal surface of which a first electrode pad and a second electrode pad are disposed, an image pickup device, a back surface disposed opposite to a light-receiving surface of which is disposed opposite to the principal surface of the chip part and a third electrode pad of which is disposed on the back surface and a wiring board including a flying lead that protrudes from an end face, in which the flying lead is inserted into a gap between the chip part and the image pickup device, the first electrode pad and the flying lead are bonded together via a first bump, the bonded portion is sealed with first sealing resin, the second electrode pad and the third electrode pad are bonded together via a second bump higher than the first bump and a space of the gap not sealed with the first sealing resin is sealed with second sealing resin having a lower Young's modulus than a Young's modulus of the first sealing resin.

As has already been described, since the image pickup unit 1 or the like has a small diameter, the diameter of the insertion portion 80 of the endoscope 9 can be easily reduced. In the image pickup unit 1 or the like, since the bonding strength between the first electrode pad 32 and the flying lead 41 is strong, both parts are never detached from each other when the image pickup unit 1 is disposed at the distal end portion 81. For this reason, the endoscope 9 can be manufactured easily and achieve high manufacturing yield.

<Electronic Unit>

Figure 9:
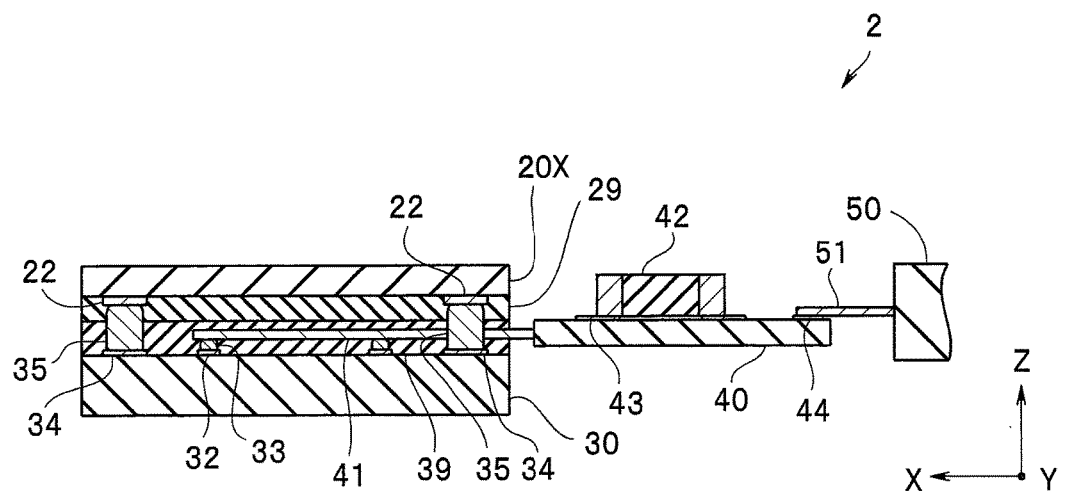
FIG. 9 is a cross-sectional view of an electronic unit according to an embodiment.

Next, FIG. 9 illustrates an electronic unit 2 according to another embodiment. Since the electronic unit 2 is similar to the image pickup unit 1 or the like, the same components are assigned the same reference numerals and description is omitted. Unlike the image pickup unit 1 or the like, the electronic unit 2 has no image pickup device in which a light-receiving section is formed, but the electronic unit 2 has the same effects as the effects of the image pickup unit 1 or the like.

That is, the electronic unit 2 includes a first wiring chip 30, on a principal surface of which a first electrode pad 32 and a second electrode pad 34 are disposed, a second chip part 20X, a back surface of which is disposed opposite to a front face of the first chip part 30 and on a back surface of which a third electrode pad 22 is disposed and a wiring board 40 including a flying lead 41 that protrudes from an end face, in which the flying lead 41 is inserted into a gap between the first wiring chip 30 and the second chip part 20X, the first electrode pad 32 and the flying lead 41 are bonded together via the first bump 33, the bonded portion is sealed with first sealing resin 39, the second electrode pad 34 and the third electrode pad 22 are bonded together via a second bump 35 which is higher than the first bump 33 and a space of the gap not sealed with the first sealing resin 39 is sealed with second sealing resin 29.

It is preferable that the first sealing resin 39 and the second sealing resin 29 be thermosetting resin, a curing temperature of the first sealing resin 39 be higher than a curing temperature of the second sealing resin 29 and a glass transition temperature of the first sealing resin 39 be higher than a curing temperature of the second sealing resin 29.

Furthermore, a Young's modulus of the first sealing resin 39 is preferably 10 GPa or higher and a Young's modulus of the second sealing resin 29 is preferably 5 GPa or lower.

A method for manufacturing the electronic unit 2 includes a step of manufacturing a first chip part 30, on a principal surface of which a first electrode pad 32 and a second electrode pad 34 are disposed, a second chip part 20, on a back surface of which a third electrode pad 22 is disposed and a wiring board 40 including a flying lead 41 that protrudes from an end face, a step of bonding the first electrode pad 32 of the first chip part 30 and the flying lead 41 of the wiring board 40 via a first bump 33, a step of sealing the bonded portion between the first electrode pad 32 and the flying lead 41 with first sealing resin 39, a step of curing the first sealing resin 39 at a first temperature, a step of disposing the principal surface of the first chip part 30 and the back surface of the second chip part 20 opposite to each other and bonding the second electrode pad 34 and the third electrode pad 22 via a second bump 35 which is higher than the first bump 33, a step of injecting second sealing resin 29 into a gap between the principal surface of the first chip part 30 and the back surface of the second chip part 20 and a step of curing the second sealing resin 29 at a temperature lower than the first temperature and lower than a glass transition temperature of the first sealing resin 39.

In the above-described respective embodiments, the first sealing resin and the second sealing resin are used to reduce stress caused by a difference in a thermal expansion coefficient between the first chip part and the second chip part, but if there is no need to reduce such stress, sealing may be performed using only the first sealing resin instead of using both the first sealing resin and the second sealing resin.

The present invention is not limited to the aforementioned embodiments or the like, but the present invention can be changed, combined or applied in various ways without departing from the spirit and scope of the present invention.

What is claimed is:

1. An endoscope comprising an image pickup unit at a distal end of an insertion portion, the image pickup unit comprising:
   a chip part, on a principal surface of which a first electrode pad and a second electrode pad are disposed;
   an image pickup device, a back surface opposite to a light-receiving surface of which is disposed opposite to the principal surface of the chip part and on the back surface of which a third electrode pad is disposed; and
   at least one wiring board comprising a flying lead that protrudes from an end face, wherein
   the flying lead is inserted into a gap between the chip part and the image pickup device,
   the first electrode pad and the flying lead are bonded together via a first bump and a bonded portion between the first electrode pad and the flying lead is sealed with first sealing resin, and
   the second electrode pad and the third electrode pad are bonded together via a second bump which is higher than the first bump, and a space of the gap not sealed with the first sealing resin is sealed with second sealing resin having a Young's modulus lower than a Young's modulus of the first sealing resin.

2. An electronic unit comprising:
   a first chip part, on a principal surface of which a first electrode pad and a second electrode pad are disposed;
   a second chip part, a back surface opposite to a front surface of which is disposed opposite to the principal surface of the first chip part and on the back surface of which a third electrode pad is disposed; and
   a wiring board comprising a flying lead that protrudes from an end face, wherein the flying lead is inserted into a gap between the first chip part and the second chip part,
   the first electrode pad and the flying lead are bonded together via a first bump, and a bonded portion between the first electrode pad and the flying lead is sealed with first sealing resin, and
   the second electrode pad and the third electrode pad are bonded together via a second bump which is higher than the first bump and a space of the gap not sealed with the first sealing resin is sealed with second sealing resin.

3. The electronic unit according to claim 2, wherein
   the first sealing resin and the second sealing resin are thermosetting resin,
   a curing temperature of the first sealing resin is higher than a curing temperature of the second sealing resin, and
   a glass transition temperature of the first sealing resin is higher than a curing temperature of the second sealing resin.

4. The electronic unit according to claim 3, wherein
   a Young's modulus of the first sealing resin is 10 GPa or higher, and
   a Young's modulus of the second sealing resin is lower than 10 GPa.

5. The electronic unit according to claim 2, wherein
   the first chip part is a wiring chip that connects the first electrode pad and the second electrode pad,
   the second chip part is an image pickup device, the front face opposite to the back surface of which is a light-receiving surface, and
   a signal cable is bonded to an end portion of the wiring board.

6. The electronic unit according to claim 2, wherein
   the first chip part is a first wiring chip configured to connect the first electrode pad and the second electrode pad,
   the second chip part is a second wiring chip configured to connect an image pickup device disposed on the front face and the first wiring chip, and
   a signal cable is bonded to an end portion of the wiring board.

7. The electronic unit according to claim 5, wherein
   the electronic unit is a horizontal image pickup unit comprising a prism disposed on the light-receiving surface of the image pickup device.

8. The electronic unit according to claim 5, wherein
   the electronic unit is a vertical image pickup unit in which the flying lead is bent at a right angle outside the gap and the wiring board is disposed perpendicular to the light-receiving surface.

9. The electronic unit according to claim 8, further comprising two units of the wiring board, wherein the two units of the wiring board are disposed opposite to each other so as to sandwich the first chip part and the second chip part in between.

10. A method for manufacturing an electronic unit comprising:
    a step of manufacturing a first chip part, on a principal surface of which a first electrode pad and a second electrode pad are disposed, a second chip part, on a back surface opposite to a front surface of which a third electrode pad is disposed, and a wiring board comprising a flying lead that protrudes from an end face;
    a step of bonding the first electrode pad of the first chip part and the flying lead of the wiring board via a first bump;
    a step of sealing a bonded portion between the first electrode pad and the flying lead with first sealing resin;
    a step of curing the first sealing resin at a first temperature;
    a step of disposing the principal surface of the first chip part and the back surface of the second chip part opposite to each other and bonding the second electrode pad and the third electrode pad via a second bump which is higher than the first bump;
    a step of injecting second sealing resin into a gap between the principal surface of the first chip part and the back surface of the second chip part; and
    a step of curing the second sealing resin at a temperature lower than the first temperature and lower than a glass transition temperature of the first sealing resin.

11. The method for manufacturing an electronic unit according to claim 10, wherein
    a Young's modulus of the first sealing resin is 10 GPa or higher, and
    a Young's modulus of the second sealing resin is lower than 10 GPa.

12. The method for manufacturing an electronic unit according to claim 10, wherein the first chip part is a wiring chip configured to connect the first electrode pad and the second electrode pad, the second chip part is an image pickup device, a front face opposite to the back surface of which is a light-receiving surface, and a signal cable is bonded to an end portion of the wiring board.

13. The method for manufacturing an electronic unit according to claim 10, wherein the first chip part is a first wiring chip configured to connect the first electrode pad and the second electrode pad, the second chip part is a second wiring chip configured to connect an image pickup device disposed on the front face and the first wiring chip, and a signal cable is bonded to an end portion of the wiring board.

14. The method for manufacturing an electronic unit according to claim 10, further comprising, after the step of curing the second sealing resin, a step of bending the flying lead at a right angle outside the gap between the first chip part and the second chip part and disposing the wiring board perpendicular to the principal surface of the first chip part.

* * * * *